(12) United States Patent
Zhang et al.

(10) Patent No.: US 8,277,700 B2
(45) Date of Patent: Oct. 2, 2012

(54) PROCESS FOR PREPARING A PHOTOCHROMIC POLYMERIC COMPOSITION, THUS OBTAINED POLYMERIC COMPOSITION AND USE THEREOF

(75) Inventors: Zhengfeng Zhang, Shanghai (CN); Wentian Lan, Jiangsu (CN)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 13/131,441

(22) PCT Filed: Nov. 20, 2009

(86) PCT No.: PCT/EP2009/065545
§ 371 (c)(1),
(2), (4) Date: May 26, 2011

(87) PCT Pub. No.: WO2010/066555
PCT Pub. Date: Jun. 17, 2010

(65) Prior Publication Data
US 2011/0260125 A1   Oct. 27, 2011
US 2012/0085980 A2   Apr. 12, 2012

(30) Foreign Application Priority Data
Dec. 8, 2008   (WO) ................ PCT/CN2008/073370

(51) Int. Cl.
*G02B 5/23*   (2006.01)
*G02C 7/02*   (2006.01)
(52) U.S. Cl. ......... 252/586; 8/507; 351/159; 351/160 R; 351/162; 523/106; 544/71
(58) Field of Classification Search ................ 250/492.1; 252/582, 586; 351/160 R, 162, 163, 159; 427/559; 428/423.5, 423.1, 424.2; 523/106, 523/107; 524/201; 544/71; 8/507
See application file for complete search history.

(56) References Cited

U.S. PATENT DOCUMENTS

| | | | |
|---|---|---|---|
| 2003/0044620 A1* | 3/2003 | Okoroafor et al. | 428/423.5 |
| 2005/0254003 A1 | 11/2005 | Jani et al. | |
| 2005/0269556 A1 | 12/2005 | Evans et al. | |
| 2008/0006798 A1 | 1/2008 | Evans et al. | |
| 2008/0018853 A1* | 1/2008 | Jethmalani et al. | 351/163 |
| 2009/0250670 A1* | 10/2009 | Kim et al. | 252/586 |

FOREIGN PATENT DOCUMENTS
WO   2004 041961   5/2004

OTHER PUBLICATIONS
International Search Report issued Aug. 23, 2010 in PCT/EP09/65545 filed Nov. 20, 2009.

\* cited by examiner

*Primary Examiner* — Bijan Ahvazi
(74) *Attorney, Agent, or Firm* — Oblon, Spivak, McClelland, Maier & Neustadt, L.L.P.

(57) ABSTRACT

The present invention discloses a process for preparing a photochromic polymeric composition, characterized in that the photochromic polymeric composition is prepared by comprising (meth)acrylamide compound in the reaction mixture useful for the preparation of the photochromic polymeric composition. The present invention also relates to the thus obtained polymeric composition, photochromic articles made from said polymeric composition, and use of said polymeric composition for preparing photochromic articles. The photochromic polymeric composition according to the present invention makes the absorption peak of the photochromic dye therein become longer, thus exhibiting a desired grey with a bit bluish green or grey with a bit blue.

18 Claims, No Drawings

PROCESS FOR PREPARING A PHOTOCHROMIC POLYMERIC COMPOSITION, THUS OBTAINED POLYMERIC COMPOSITION AND USE THEREOF

TECHNICAL FIELD

The present invention relates to a process for preparing a photochromic polymeric composition, to the thus obtained polymeric composition, to photochromic articles made from the photochromic polymeric composition prepared by the process according to the present invention, and to the use of the photochromic composition prepared by the process according to the present invention for manufacturing photochromic articles.

BACKGROUND ART

Photochromism is a well-known physical phenomenon, which is observed with certain classes of compounds. Under irradiation of polychromatic light or monochromatic light, photochromic dyes will turn from colorless into colored or from one color into another color. When the irradiation is removed, or under different irradiation from the first polychromatic light or monochromatic light, photochromic dyes will change back to their original colors. A detailed description of this phenomenon can be found in "Photochromism: Molecules and systems", Studies in Organic Chemistry 40, Eds. H. Durr and H. Bouas-Laurent, Elsevier, 1990.

It is well known that 2H-naphtho[1,2-b]pyran compounds are capable of exerting a photochromic effect. For example, U.S. Pat. No. 4,826,977 describes a series of yellow/orange coloring 2H-naphtho[1,2-b]pyrans containing a spiro-adamantane group at the 2-position, and isomeric naphthopyran systems. In addition, a range of purple/blue coloring 2-(4-aminophenyl)-2-alkyl-2H-naphtho[1,2-b]pyrans have also been disclosed in U.S. Pat. No. 4,818,096.

A disadvantage of the present naphthopyran compounds lies in that their wavelength for the photochromic effect is not long enough, which means that the resulting color is not the ideal green or bluish green. The currently available naphthopyran on the market with the longest wavelength is the product of company JAMES ROBINSON with the trade name REVERSACOL GRAPHITE. However, the first absorption peak $\lambda_{max}$ of said product in toluene is 486 nm, and the second one $\lambda_{max}$ in toluene is 593 nm, wherein only the first $\lambda_{max}$ plays a major role.

As described above, an ideal commercial photochromic lens is supposed to take on a color of grey with a bit bluish green in the sun. The common solution to this problem is to use naphthopyrans in combination with naphthoxazines. An example of said naphthoxazines is the product by JAMES ROBINSON with the trade name REVRSACOL SEA GREEN. But the naphthoxazine compound has a rather poor heat resistance: when temperature is higher than 40° C., its photochromic effect decreases drastically and cannot be used in combination with the naphthopyran compound.

US 2005/0254003 discloses a process for preparing a photochromic polymeric composition. The invention provides polymers having photochromic property and being capable of filtering at least a portion of blue light incident thereon within sufficient mechanical properties.

Therefore, people attempt to solve the aforesaid technical problem, that is, to make the absorption wavelength of the naphthopyran photochromic compound longer, and moreover to retain a good heat resistance. A traditional method to this end is to change the substituent(s) of the naphthopyran compound. However, the resultant product cannot ensure that the effect of absorption wavelength red shift could be achieved as expected after mixing the dyes with the polymer matrix to form articles.

DISCLOSURE OF THE INVENTION

In view of the above-identified problems existing in the prior art, the inventors of the present invention have carried out extensive and profound research in the field of photochromic polymeric materials, and surprisingly found out that said technical problem could be solved when a small amount of (meth)acrylamide compound is incorporated into the traditional photochromic composition formulation. The photochromic polymeric composition prepared in such a way not only possesses the color of grey with a bit bluish green or grey with a bit blue, but also retains a good heat resistance of the photochromic compound.

According to the first aspect, the present invention provides a process for preparing a photochromic polymeric composition, wherein a reaction mixture M comprising the following components (A), (B) and (C)

(A) 0.1-20 wt. % of one or more compounds of the formula (I)

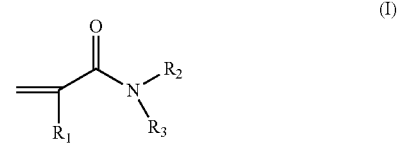

(I)

in which,
$R_1$ is hydrogen or methyl,
$R_2$ is hydrogen or $C_1$-$C_5$-alkyl, and
$R_3$ is hydrogen, $C_1$-$C_5$-alkyl, $C_1$-$C_5$-alkoxy, butoxymethyl or $C_1$-$C_8$-alkalkylamine, (B) 80-99.9 wt. % of a polymerizable component, and
(C) 0.001-1 wt. % of a photochromic dye,
is polymerized so as to obtain said photochromic polymeric composition.

In the process of the present invention, in order to obtain the photochromic polymeric composition, one or more particular (meth)acrylamide compounds of the formula (I) are used. The use of said compounds results in a longer wavelength of the photochromic dye in the obtained photochromic polymeric composition, so that the desired color of grey with a bit bluish green or grey with a bit blue is achieved. The prior arts do not disclose that the inventive photochromic polymeric composition prepared according to the inventive process has longer wavelength for the photochromic effect and a better heat resistance by incorporating a small amount of the compound of the formula (I) into the traditional photochromic composition formulation.

In the context of the present invention, $C_1$-$C_5$-alkyl should be understood as straight chain or branched-chain alkyl containing from 1 to 5 carbon atoms, and examples thereof include methyl, ethyl, n-propyl, iso-propyl, n-butyl, iso-butyl, sec-butyl, tert-butyl, n-pentyl, iso-pentyl, sec-pentyl and neo-pentyl, preferably methyl and ethyl.

In the context of the present invention, $C_1$-$C_5$-alkoxy should be understood as $C_1$-$C_5$-alkyl connected to an oxygen atom, namely, $C_1$-$C_5$-alkyl-O—, wherein the definition of the $C_1$-$C_5$-alkyl herein is completely identical with that of the $C_1$-$C_5$-alkyl as set forth in the previous paragraph. Examples of said $C_1$-$C_5$-alkoxy include methoxy, ethoxy, n-propoxy, iso-propoxy, n-butoxy, iso-butoxy, sec-butoxy, tert-butoxy, n-pentoxy, iso-pentoxy, sec-pentoxy and neo-pentoxy, preferably methoxy, ethoxy, n-propoxy and n-butoxy.

In the reaction mixture M used in the process according to the present invention, the compound of the formula (I) is preferably one or more selected from the group consisting of acrylamide, methacrylamide (MAA), N-methoxy-acrylamide, N-methoxy-methacrylamide, N-butoxy-methacrylamide, N-butoxymethyl-methacrylamide (N-BMMAA), N-isopropyl-acrylamide and N-isopropyl-methacrylamide (NIPMAA). More preferably, the compound of formula (I) is acrylamide, methacrylamide, or NIPMAA, or any combination of said three compounds.

Based on the total weight of the reaction mixture M, the amount of the compound of the formula (I) used in the reaction mixture M is generally 0.1-20 wt. %, preferably 0.5-15 wt. %, more preferably 1-6 wt. %, and particularly preferable 3-5 wt. %.

According to the present invention, the compound of the formula (I) could be added in the form of solid or liquid. If the compound is liquid, it may be added directly, and of course may also be added in the form of mixture with monomer(s) for polymerization commonly used to prepare the photochromic polymeric composition (said monomers are included within the polymerizable component according to the present invention). If the compound is solid, it may be dissolved or dispersed in monomer(s) for polymerization commonly used to prepare the photochromic polymeric composition (said monomers are included within the polymerizable component according to the present invention), or may be dissolved or dispersed in auxiliary monomer(s) in which the compound of the formula (I) has a good solubility. Said auxiliary monomer aims at dissolving the compound of the formula (I), and in the process according to the present invention, it may either be polymerized or not be polymerized, and preferably it may be polymerized. Suitable auxiliary monomer is, for example β-hydroxyethyl methacrylate (HEMA), acrylonitrile, methyl methacrylate, ethyl methacrylate, iso-butyl methacrylate, methacrylic acid, styrene and/or acetone. For instance, methacrylamide (MMA), which accounts for 1-3 wt. % of the total amount of the reaction mixture M, may be directly dissolved in the commonly used monomer for polymerization, E2BADMA/E4BADMA (ethoxylated bisphenol-A dimethacrylates with 2 or 4 repeating units of ethoxy, respectively) or PEG400DMA (polyethylene glycol di(meth)acrylate with the PEG molecule weight of about 400). But it is preferred to dissolve MAA in HEMA, and mix the resultant with the commonly used monomer(s) for polymerization, E2BADMA/E4BADMA or PEG400DMA, etc.

In the processes of the present invention, in order to obtain the photochromic polymeric composition, a polymerizable component is used. Said component aims to form the polymeric matrix of the photochromic polymeric composition. For the purpose of the present invention, suitable polymerizable component includes $C_1$-$C_{30}$-alkyl (meth)acrylates, examples thereof including: methyl (meth)acrylate, ethyl (meth)acrylate, butyl (meth)acrylate, cyclohexyl (meth)acrylate, isobornyl (meth)acrylate, trimethyl cyclohexyl (meth) acrylate. The polymerizable component also includes hydroxyethyl (meth)acrylate, hydroxypropyl (meth)acrylate, hydroxybutyl (meth)acrylate, benzyl (meth)acrylate, ethylene glycol di(meth)acrylate. The polymerizable component additionally includes ethoxylated phenol (meth)acrylates, for example ethoxylated bisphenol-A dimethacrylates with 2 to 10 repeating units of ethoxy, namely, $E_{2-10}$BADMA, such as, E2BADMA, E3BADMA (an ethoxylated bisphenol-A dimethacrylate with 3 repeating units of ethoxy) and E4BADMA; polyethylene glycol di(meth)acrylate with 2 to 25 repeating units of ethylene glycol, examples thereof including PEG400DMA, PEG200DMA with the respective PEG molecule weights of about 400 and 200; and styrene. In the process of the present invention, the polymerizable component may be used as either a single one of the above-identified polymerizable components or a combination of at least two of them.

Based on the total weight of the reaction mixture M, the amount of the polymerizable component used in the reaction mixture M is generally 80-99.9 wt. %, preferably 85-99.5 wt %, more preferably 94-99 wt. %, and particularly preferably 95-97 wt. %.

In the process of the present invention, in order to obtain the photochromic polymeric composition, a photochromic dye is used. Said photochromic dye is preferably selected from naphthopyran photochromic dyes. More preferably, said photochromic dye is naphthopyran photochromic dye represented by the formulae (II) and/or (III):

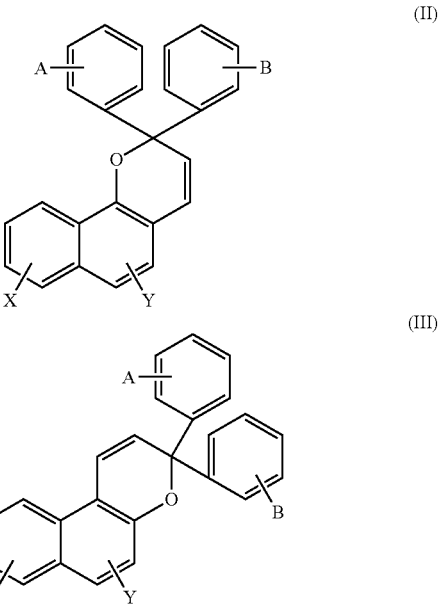

in which, variables A, B, X, and Y in the formula (II) are each independently represent $C_1$-$C_5$-alkyl or $C_1$-$C_5$-alkoxy, and variables A, B, X and Y in the formula (III) are also each independently represent $C_1$-$C_5$-alkyl or $C_1$-$C_5$-alkoxy. Terms "$C_1$-$C_5$-alkyl" and "$C_1$-$C_5$-alkoxy" herein have the meanings as shown above.

The photochromic dyes especially suitable for the present invention are those naphthopyran compounds having an absorption peak at around 550 nm; in particular the products provided by JAMES ROBINSON (UK) with the trade names REVERSACOL° GRAPHITE, REVERSACOL® heather, REVERSACOL® MidnightGrey and REVERSACOL® MistyGrey, wherein REVERSACOL® GRAPHITE or REVERSACOL® MidnightGrey, or the combination of these two is very particularly preferred.

In the process according to the present invention, in order to prepare the photochromic polymeric composition, one or more of the aforesaid photochromic dyes may be used, and the use of only one photochromic dye is preferred.

Based on the total weight of the reaction mixture M, the amount of the photochromic dye used in the reaction mixture M is generally 0.001-1 wt. %, preferably 0.01-1 wt. %, more preferably 0.01-0.05 wt. %, and particularly preferably 0.015-0.035 wt. %.

In order to prepare the photochromic polymeric composition according to the present invention, the reaction mixture M containing components (A)-(C) of the present invention is required to be polymerized, so that said photochromic polymeric composition is obtained. Generally, said polymerization is carried out in the presence of a free radical initiator. The free radical initiator may be any conventional initiator used for free radical polymerization. It is preferred that said free radical initiator is an azo compound, and examples thereof include azobisisobutyronitrile (AIBN), 2,2'-azobis(2-methylbutyronitrile) (AMBN) and 2,2'-azobis(2,4-dimethylvaleronitrile) (ADVN), which are available from Akzo Nobel Chemical, Inc. In the process of the present invention, the used free radical initiator is preferably AIBN, AMBN or ADVN.

In the process of the present invention, the amount of the initiator used to initiate the polymerization of the reaction mixture M is conventional, and depends on, e.g. initiation efficiency or activity of the initiators per se. Generally, based on the total weight of the reaction mixture M, the amount of the initiator used is generally 0.01-1 wt. %, preferably 0.01-0.5 wt. %, more preferably 0.1-0.5 wt. %, particularly preferably 0.15-0.35 wt. %.

In the process of the present invention, the method for polymerizing the reaction mixture M to obtain the inventive photochromic polymeric composition is not particularly limited, as long as the inventive photochromic polymeric composition could be obtained by means of it. For example, said polymerization method includes bulk polymerization, solution polymerization, etc.

In the process according to the present invention, the process conditions for reacting the reaction mixture M to obtain the inventive photochromic polymeric composition are conventional with respect to the preparation of a photochromic polymeric composition. Generally, said reaction may be carried out for 0.5-50 hours at a temperature of 10-220° C., obtaining the photochromic polymeric composition according to the present invention. Said reaction preferably takes place in stages. For instance, it may be conducted as follows: the reaction mixture is heated for 2-10 hours at 25° C.-45° C., and then heated for another 2-10 hours at 50-80° C., and subsequently heated for further 2-10 hours at 80-90° C., and then cooled to 50-80° C. and maintained at this temperature for 0.5-3 hours; preferably, the reaction mixture is heated for 4-5 hours at a temperature of 25° C.-45° C., then heated for another 4-5 hours at a temperature of 60-70° C., subsequently heated for further 4-5 hours at a temperature of 80-90° C., and then cooled to 60-70° C. and maintained at this temperature for 1-2 hours.

In the process of the present invention, in order to make the photochromic dye distribute in the resultant photochromic polymeric composition as uniformly as possible, it is preferred to initiate the polymerization reaction only after the photochromic dye contained in the reaction mixture dissolves substantially or sufficiently. In order to make the photochromic dye dissolve sufficiently, stirring and/or heating may be usually adopted. For example, the reaction mixture M is fully stirred (generally for several hours, e.g. 2, 3 or 4 hours) prior to increasing its temperature to a certain degree, e.g. to 45-55° C., preferably around 55° C.

In one preferred embodiment of the process according to the present invention, said process may be conducted as follows: 55-65% of one or more compounds selected from the group consisting of E2BADMA, E3BADMA and E4BADMA, 35-45% of one or more compounds selected from the group consisting of PEG400DMA and PEG200DMA, 1-5% of HEMA, 1-5% of MAA, and 0.01-0.1% of REVERSACOL® GRAPHITE or REVERSACOL® MidnightGrey are mixed at a temperature of 10-50° C. to get the dye dissolved fully, then 0.15% of ADVN or AIBN is added to the resulting mixture, and it is followed by filling into a mold, and reacting at 25-45° C. for 5 hours, at 60-70° C. for another 5 hours, and then at 80-90° C. for further 5 hours and then cooled to 60-70° C. and maintained at this temperature for 1-2 hours.

In order to make the photochromic polymeric composition prepared by the process of the present invention more colorful, one or more non-photochromic colorants capable of adjusting color could be incorporated during preparing the photochromic polymeric composition according to the present invention. Said colorants may be not only dyes but also pigments. These dyes and/or pigments are conventional for the photochromic polymeric materials, and could be selected by a person skilled in the art according to concrete situations. The timing of adding said non-photochromic colorants is conventional for a person skilled in the art, and they could be added at any time during polymerization. For instance, said colorants may either be contained in the reaction mixture M as starting material prior to polymerization, or be incorporated into the reaction mixture after the polymerization has begun. It is preferred to comprise said colorants in the reaction mixture M as starting material prior to polymerization.

In order to improve the durability of the photochromic polymeric composition prepared by the process of the present invention, the following substances may also be added during the preparation of the photochromic polymeric composition of the present invention:
  one or more stabilizers, such as anti-oxidants,
  and/or one or more anti-UV agents, including hindered amine light stabilizers (HALS), such as Tinuvin 770,
  and/or one or more anti-radical agents,
  and/or one or more photochromic excited state deactivators.

All the above-identified additives are conventional for photochromic polymeric materials, and a person skilled in the art is able to freely select the types and amount of these additives according to concrete situations. Besides, the timing of adding said additives is also conventional for a person skilled in the art, and they may be added at any time during polymerization. For example, they may either be contained in the reaction mixture M as starting material prior to polymerization, or be incorporated into the reaction mixture after the polymerization has begun. It is preferred to comprise these additives in the reaction mixture M as starting material before prior to polymerization.

The photochromic polymeric composition prepared according to the present invention makes the absorption wavelength of the photochromic dye (naphthopyran photochromic dyes in particular) therein shift and become longer, which causes the obtained photochromic polymeric composition to exhibit an expected color of grey with a bit blue or grey with a bit bluish green. At present, the inventors are not sure about the exact mechanism that the addition of a small amount of (meth)acrylamide compounds of the formula (I) of the present invention into the traditional photochromic composition formulation could enable the absorption wavelength of the inclusive photochromic dye to become longer.

According to the second aspect, the present invention relates to a photochromic polymeric composition prepared by the process of the present invention.

According to the third aspect, the present invention also relates to photochromic articles made from the photochromic polymeric composition prepared by the process of the present invention or from the photochromic polymeric composition of the present invention. Said articles especially include optical elements, such as sunglasses, ophthalmic lenses (including vision correcting lenses and plano lenses), window glass (particularly the window glass of architectures, trains and cars), transparent polymer sheets, automatically photochromic windshields, aircraft transparencies, and decoration materials for building.

Finally, the present invention also relates to the use of the photochromic polymeric composition prepared by the process of the present invention or the photochromic polymeric composition of the present invention for manufacturing the photochromic articles.

As to the above-mentioned use and photochromic articles of the present invention, the photochromic polymeric composition prepared by the process of the present invention, after the completion of the polymerization, per se may constitute the photochromic articles. For example, by means of reactive casting, the reaction mixture M of the present invention is poured into the mold for polymerization, especially for bulk polymerization, and the photochromic articles may be immediately obtained after polymerization. The photochromic polymeric composition prepared by the process of the present invention or the photochromic polymeric composition of the present invention may also be further comprised in other polymer matrix so as to obtain the photochromic articles by means of conventional forming technology in the field of polymer processing.

The present invention will be illustrated by the following Examples; however, in any case, these Examples should not be explained as a limitation on the scope of the present invention.

EXAMPLES

The formulations of the following Examples are shown in the table 1 below, in which the amounts of the components contained in each formulations are all presented by weight percent.

of E4BADMA, 37.600 wt. % of PEG400DMA, 3.000 wt. % of HEMA, 3.000 wt. % of MAA and 0.035 wt. % of REVERSACOL® GRAPHITE.

Then the resultant mixture was heated to 50° C. in order to make REVERSACOL® GRAPHITE dissolve fully. This was followed by reducing the temperature to 30° C., adding 0.150 wt. % of ADVN into the mixture, and stirring uniformly. After ADVN had been dissolved, the temperature was reduced to 25° C. Then the mixture after degassing was injected into the mold.

Then the filled mold was heated at a temperature of 25° C.-45° C. for 5 hours, then heated at 65° C. for another 5 hours and afterwards heated at 85° C. for further 5 hours. After that it was cooled to 65° C. and maintained at this temperature for 1 hour.

The mold was then dissembled and the resultant photochromic lens was maintained at 110° C. for 2 hours.

The lens has a first absorption peak $\lambda_{max}$ at 506 nm and a second absorption peak $\lambda_{max}$ at 613 nm. Moreover, said lens took on a color of grey with a bit bluish green.

Example 2

Two pieces of glasses were assembled with a liquid tight gasket which had already been cleaned, and fixed with the help of a clamp, resulting in a mold, for use. The following components were uniformly mixed for 3 hours: 57.415 wt. % of E4BADMA, 38.400 wt. % of PEG400DMA, 3.000 wt. % of HEMA, 1.000 wt. % of MAA and 0.035 wt. % of REVERSACOL® GRAPHITE.

Then the resultant mixture was heated to 50° C. in order to make REVERSACOL® GRAPHITE dissolve fully. This was followed by reducing the temperature to 30° C., adding 0.150 wt. % of ADVN into the mixture, and stirring uniformly. After ADVN had been dissolved, the temperature was reduced to 25° C. Then the mixture after degassing was injected into the mold.

TABLE 1

| | | Example 1 | Example 2 | Example 3 | Comparative Example 4 | Example 5 |
|---|---|---|---|---|---|---|
| Polymerizable component | E4BADMA | 56.215 | 57.415 | 55.015 | 58.015 | 55.935 |
| | PEG200DMA | | | | | 37.400 |
| | PEG400DMA | 37.600 | 38.400 | 36.800 | 38.800 | |
| Auxiliary monomer | HEMA | 3.000 | 3.000 | 3.000 | 3.000 | 3.000 |
| Compound of formula (I) | MAA | 3.000 | 1.000 | 5.000 | — | — |
| | NIPMAA | — | — | — | — | 3.000 |
| Photochromic dye | | REVERSACOL ® GRAPHITE 0.035 | REVERSACOL ® GRAPHITE 0.035 | REVERSACOL ® GRAPHITE 0.035 | REVERSACOL ® GRAPHITE 0.035 | REVERSACOL ® Midnight Grey 0.015 |
| Initiator | | ADVN 0.150 | ADVN 0.150 | ADVN 0.150 | ADVN 0.150 | AIBN 0.150 |
| Anti-UV stabilizer | | | | | | HALS Tinuvin770 0.500 |
| $\lambda_{max}$ | $1^{st} \lambda_{max}$ | 506 | 499 | 508 | 496 | 506 |
| | $2^{nd} \lambda_{max}$ | 613 | 606 | 615 | 603 | 613 |
| Color | | Grey with a bit bluish green | Grey with a bit blue | Grey with a bit bluish green | Grey | Grey with a bit blue |

Example 1

Two pieces of glasses were assembled with a liquid tight gasket which had already been cleaned, and fixed with the help of a clamp, resulting in a mold, for use. The following components were uniformly mixed for 3 hours: 56.215 wt. %

Then the filled mold was heated at a temperature of 25° C.-45° C. for 5 hours, then heated at 65° C. for another 5 hours and afterwards heated at 85° C. for further 5 hours. After that it was cooled to 65° C. and maintained at this temperature for 1 hour.

The mold was then dissembled and the resultant photochromic lens was maintained at 110° C. for 2 hours.

The lens has a first absorption peak $\lambda_{max}$ at 499 nm and a second absorption peak $\lambda_{max}$ at 606 nm. Moreover, said lens took on a color of grey with a bit blue.

Example 3

Two pieces of glasses were assembled with a liquid tight gasket which had already been cleaned, and fixed with the help of a clamp, resulting in a mold, for use. The following components were uniformly mixed for 3 hours: 55.015 wt. % of E4BADMA, 36.800 wt. % of PEG400DMA, 3.000 wt. % of HEMA, 5.000 wt. % of MAA and 0.035 wt. % of REVERSACOL® GRAPHITE.

Then the resultant mixture was heated to 50° C. in order to make REVERSACOL® GRAPHITE dissolve fully. This was followed by reducing the temperature to 30° C., adding 0.150 wt. % of ADVN into the mixture, and stirring uniformly. After ADVN had been dissolved, the temperature was reduced to 25° C. Then the mixture after degassing was injected into the mold.

Then the filled mold was heated at a temperature of 25° C.-45° C. for 5 hours, then heated at 65° C. for another 5 hours and afterwards heated at 85° C. for further 5 hours. After that it was cooled to 65° C. and maintained at this temperature for 1 hour.

The mold was then dissembled and the resultant photochromic lens was maintained at 110° C. for 2 hours.

The lens has a first absorption peak $\lambda_{max}$ at 508 nm and a second absorption peak $\lambda_{max}$ at 615 nm. Moreover, said lens took on a color of grey with a bit bluish green.

Comparative Example 4

Two pieces of glasses were assembled with a liquid tight gasket which had already been cleaned, and fixed with the help of a clamp, resulting in a mold, for use. The following components were uniformly mixed for 3 hours: 58.015 wt. % of E4BADMA, 38.800 wt. % of PEG400DMA, 3.000 wt. % of HEMA, and 0.035 wt. % of REVERSACOL® GRAPHITE.

Then the resultant mixture was heated to 50° C. in order to make REVERSACOL® GRAPHITE dissolve fully. This was followed by reducing the temperature to 30° C., adding 0.150 wt. % of ADVN into the mixture, and stirring uniformly. After ADVN had been dissolved, the temperature was reduced to 25° C. Then the mixture after degassing was injected into the mold.

Then the filled mold was heated at a temperature of 25° C.-45° C. for 5 hours, then heated at 65° C. for another 5 hours and afterwards heated at 85° C. for further 5 hours. After that it was cooled to 65° C. and maintained at this temperature for 1 hour.

The mold was then dissembled and the resultant photochromic lens was maintained at 110° C. for 2 hours.

The lens has a first absorption peak $\lambda_{max}$ at 496 nm and a second absorption peak $\lambda_{max}$ at 603 nm. Moreover, said lens took on a color of grey.

Example 5

Two pieces of glasses were assembled with a liquid tight gasket which had already been cleaned, and fixed with the help of a clamp, resulting in a mold, for use. The following components were uniformly mixed for 3 hours: 55.935 wt. % of E4BADMA, 37.400 wt. % of PEG200DMA, 3.000 wt. % of HEMA, 3.000 wt. % of NIPMAA and 0.015 wt. % of REVERSACOL® MidnightGrey.

Then the resultant mixture was heated to 50° C. in order to make REVERSACOL® MidnightGrey dissolve fully. This was followed by reducing the temperature to 30° C., adding 0.150 wt. % of AIBN and 0.500 wt % of HALS Tinuvin 770 (anti-UV stabilizer) into the mixture, and stirring uniformly. After AIBN had been dissolved, the temperature was reduced to 25° C. Then the mixture after degassing was injected into the mold.

Then the filled mold was heated at a temperature of 25° C.-45° C. for hours, then heated at 65° C. for another 5 hours and afterwards heated at 85° C. for further 5 hours. After that it was cooled to 65° C. and maintained at this temperature for 1 hour.

The mold was then dissembled and the resultant photochromic lens was maintained at 110° C. for 2 hours.

The lens has a first absorption peak $\lambda_{max}$ at 506 nm and a second absorption peak $\lambda_{max}$ at 613 nm. Moreover, said lens took on a color of grey with a bit bluish green.

The invention claimed is:

1. A process for preparing a photochromic polymeric composition, comprising polymerizing a reaction mixture M comprising:

(A) 0.1-20 wt. % of at least one compound of formula (I)

$$\underset{R_1}{\overset{O}{\underset{\|}{C}}}=\text{CH}-\text{C}(=O)-N(R_2)(R_3) \tag{I}$$

wherein $R_1$ is hydrogen or methyl, $R_2$ is hydrogen or $C_1$-$C_5$-alkyl, and $R_3$ is hydrogen, $C_1$-$C_5$-alkyl, $C_1$-$C_5$-alkoxy, butoxymethyl or $C_1$-$C_8$-alkylamine;

(B) 80-99.9 wt. % of a polymerizable component; and (C) 0.001-1 wt. % of a photochromic dye, so as to obtain the photochromic polymeric composition;

wherein the photochromic dye is a naphthopyran photochromic dye represented by at least one formula selected from the group consisting of formula (II) and formula (III):

(II)

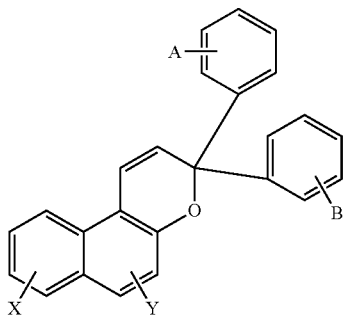

(III)

wherein, variables A, B, X, and Y in the formula (II) and (III) are each independently $C_1$-$C_5$-alkyl or $C_1$-$C_5$-alkoxy.

2. The process of claim 1, wherein the photochromic dye has an adsorption peak around 550 nm.

3. The process of claim 1, wherein the compound of formula (I) is at least one selected from the group consisting of acrylamide, methacrylamide, N-methoxy-acrylamide, N-methoxy-methacrylamide, N-butoxy-methacrylamide, N-butoxymethyl-methacrylamide, N-isopropyl-acrylamide, and N-isopropyl-methacrylamide.

4. The process of claim 1, wherein the polymerizable component is at least one selected from the group consisting of:
   a $C_1$-$C_{30}$-alkyl (meth)acrylate,
   an ethoxylated bisphenol-A dimethacrylate with 2 to 10 repeating units of ethoxy,
   a polyethylene glycol di(meth)acrylate with 2 to 25 repeating units of ethylene glycol,
   and styrene.

5. The process of claim 1, carried out in the presence of a free radical initiator.

6. The process of claim 5, wherein the free radical initiator comprises an azo initiator.

7. The process of claim 1, wherein the reaction mixture M comprises:
   (A) 0.5-15 wt. % of the at least one compound of formula (I);
   (B) 85-99.5 wt. % of the polymerizable component; and
   (C) 0.01-1 wt. % of the photochromic dye.

8. The process of claim 7, wherein the reaction mixture M comprises (A) 1-6 wt. % of the at least one compound of formula (I).

9. The process of claim 7, wherein the reaction mixture M comprises (A) 3-5 wt. % of the at least one compound of formula (I).

10. The process of claim 7, wherein the reaction mixture M comprises (B) 94-99 wt. % of the polymerizable component.

11. The process of claim 7, wherein the reaction mixture M comprises (B) 95-97 wt. % of the polymerizable component.

12. The process of claim 7, wherein the reaction mixture M comprises (C) 0.01-0.05 wt. % of the photochromic dye.

13. The process of claim 7, wherein the reaction mixture M comprises (C) 0.015-0.035 wt. % of the photochromic dye.

14. The process of claim 1, wherein component (A) is at least one selected from the group consisting of acrylamide, methacrylamide (MAA), and N-isopropyl-methacrylamide (NIPMAA),
   component (B) is at least one selected from the group consisting of ethoxylated bisphenol-A dimethacrylate with two repeating ethoxy units (E2BADMA), ethoxylated bisphenol-A dimethacrylate with three repeating ethoxy units (E3BADMA), ethoxylated bisphenol-A dimethacrylate with four repeating ethoxy units (E4BADMA), polyethylene glycol di(meth)acrylate with a PEG molecular weight of about 400 (PEG400DMA), and polyethylene glycol di(meth)acrylate with a PEG molecular weight of about 200 (PEG200DMA), and
   component (C) is at least one selected from the group consisting of a naphthopyran photochromic dye represented by at least one formula selected from the group consisting of formula (II) and formula (III):

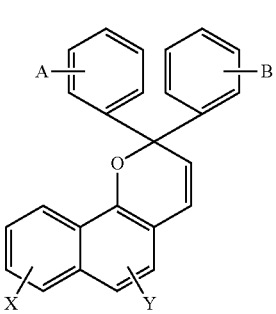

(II)

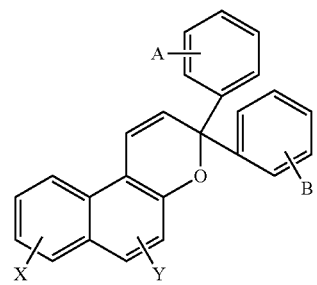

(III)

wherein, variables A, B, X, and Y in the formula (II) and (III) are each independently $C_1$-$C_5$-alkyl or $C_1$-$C_5$-alkoxy, and
the reaction mixture M further comprises β-hydroxyethyl methacrylate (HEMA) as auxiliary monomer.

15. The process of claim 14, wherein the polymerizing comprises:
   mixing
   55-65 wt. % of at least one compound selected from the group consisting of ethoxylated bisphenol-A dimethacrylate with two repeating ethoxy units (E2BADMA), ethoxylated bisphenol-A dimethacrylate with three repeating ethoxy units (E3BADMA) and ethoxylated bisphenol-A dimethacrylate with four repeating ethoxy units (E4BADMA),
   35-45 wt. % of at least one compound selected from the group consisting of polyethylene glycol di(meth)acrylate with a PEG molecular weight of about 400 (PEG400DMA) and polyethylene glycol di(meth)acrylate with a PEG molecular weight of about 200 (PEG200DMA),
   1-5 wt. % of β-hydroxyethyl methacrylate (HEMA),
   1-5 wt. % of methacrylamide (MAA), and
   0.01-0.1 wt. % of at least one naphthopyran photochromic dye represented by at least one formula selected from the group consisting of formula (II) and formula (III):

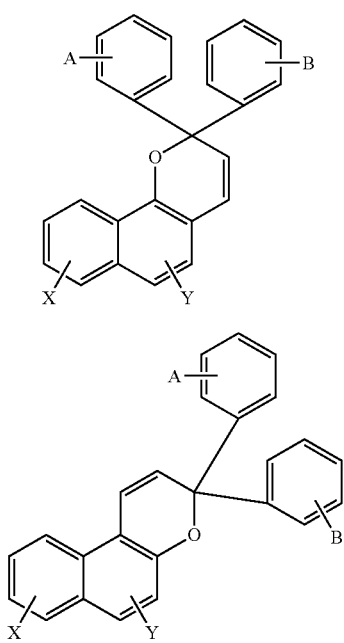

wherein, variables A, B, X, and Y in the formula (II) and (III) are each independently $C_1$-$C_5$-alkyl or $C_1$-$C_5$-alkoxy, at a temperature of 10-50° C. to fully dissolve the dye in a first resulting mixture; then adding to the first resulting mixture 0.15 wt. % of 2,2'-azobis(2,4-dimethylvaleronitrile (ADVN) or azobisisobutyronitrile (AIBN), to obtain a second resulting mixture; and, after the adding, filling the second resulting mixture into a mold;

reacting the second resulting mixture in the mold at 25-45° C. for 4-5 hours, at 60-70° C. for another 4-5 hours, and then at 80-90° C. for further 4-5 hours to obtain a third resulting mixture; and then cooling the third resulting mixture to about 60-70° C. and maintaining the third resulting mixture at this temperature for 1-2 hours.

16. The process of claim 14, wherein the naphthopyran dye has an absorption peak around 550 nm.

17. The process of claim 15, wherein the naphthopyran dye has an absorption peak around 550 nm.

18. The process of claim 1, wherein the compound of formula (I) is at least one selected from the group consisting of acrylamide, methacrylamide, and N-isopropyl-methacrylamide.

* * * * *